(12) United States Patent
Huang et al.

(10) Patent No.: US 10,650,477 B2
(45) Date of Patent: May 12, 2020

(54) LIQUID INGESTING MANAGEMENT SYSTEM

(71) Applicant: Beyond Investment Co., Ltd., Tainan (TW)

(72) Inventors: Justin Jing-Yun Huang, Tainan (TW);
Jui-Yuan Hsu, Tainan (TW);
Ching-Wei Huang, Tainan (TW);
Ching-Wu Huang, Tainan (TW);
Jean-Yun Huang, Tainan (TW);
Yu-Tung Huang, Tainan (TW)

(73) Assignee: Beyond Investment Co., Ltd., Tainan (TW)

( * ) Notice: Subject to any disclaimer, the term of this patent is extended or adjusted under 35 U.S.C. 154(b) by 389 days.

(21) Appl. No.: 14/183,531

(22) Filed: Feb. 19, 2014

(65) Prior Publication Data

US 2014/0303790 A1 Oct. 9, 2014

(30) Foreign Application Priority Data

Apr. 3, 2013 (TW) .............................. 102112198 A

(51) Int. Cl.
*G05D 9/00* (2006.01)
*G06Q 50/22* (2018.01)
*G06F 19/00* (2018.01)

(52) U.S. Cl.
CPC ......... *G06Q 50/22* (2013.01); *G06F 19/3475* (2013.01)

(58) Field of Classification Search
None
See application file for complete search history.

(56) References Cited

U.S. PATENT DOCUMENTS

| | | | | |
|---|---|---|---|---|
| 2002/0104848 A1* | 8/2002 | Burrows | ............... | A61J 7/0481 221/1 |
| 2002/0194906 A1* | 12/2002 | Goodwin | ............... | E21B 49/08 73/152.46 |
| 2006/0081653 A1* | 4/2006 | Boland | ................... | A47J 31/40 222/243 |
| 2007/0008112 A1 | 1/2007 | Covannon et al. | | |
| 2007/0062277 A1* | 3/2007 | Miller | .................... | A47G 23/14 73/428 |

(Continued)

FOREIGN PATENT DOCUMENTS

| CN | 1943810 B | 6/2010 |
|---|---|---|
| CN | 102308278 A | 1/2012 |

(Continued)

OTHER PUBLICATIONS

Chiu et al., Playful Bottle: a Mobile Social Persuasion System to Motivate Healthy Water Intake, ACM 2009, pp. 185-194.*

(Continued)

*Primary Examiner* — Diem K Cao
(74) *Attorney, Agent, or Firm* — Allen, Dyer, Doppelt + Gilchrist, PA

(57) ABSTRACT

A liquid ingesting management system is provided. The liquid ingesting management system includes a fluid container, a database and a wireless transmit/receive unit. The wireless transmit/receive unit communicates with the fluid container and the database through a wireless technique to access the database and control the fluid container to perform a liquid ingesting management process.

17 Claims, 3 Drawing Sheets

(56) References Cited

U.S. PATENT DOCUMENTS

| | | | |
|---|---|---|---|
| 2007/0146154 A1* | 6/2007 | Teller | B67D 1/1405 340/689 |
| 2007/0222619 A1* | 9/2007 | Moran | G01F 1/075 340/573.1 |
| 2010/0182518 A1* | 7/2010 | Kirmse | G06F 1/1626 348/836 |
| 2011/0108570 A1* | 5/2011 | Jarisch | A47J 31/40 99/453 |
| 2011/0180563 A1* | 7/2011 | Fitchett | B67D 3/0051 222/1 |
| 2013/0024211 A1* | 1/2013 | Monteforte | G06Q 30/0268 705/3 |
| 2014/0046596 A1* | 2/2014 | Chang | G16H 40/63 702/3 |
| 2015/0109143 A1* | 4/2015 | Hershberger | G06Q 10/08 340/870.07 |
| 2015/0245723 A1* | 9/2015 | Alexander | A47G 19/027 99/483 |
| 2016/0034663 A1* | 2/2016 | Nino | G06Q 10/10 705/2 |
| 2016/0097577 A1* | 4/2016 | Lauchnor | F25D 29/00 62/185 |

FOREIGN PATENT DOCUMENTS

| | | |
|---|---|---|
| JP | 2006-251871 A | 9/2006 |
| JP | 3132456 U | 6/2007 |
| JP | 2008-293324 A | 12/2008 |
| JP | 2011-232929 A | 11/2011 |
| TW | 200307571 A | 12/2003 |

OTHER PUBLICATIONS

Masanori Ueda et al., Development of the Coaster type Sensing Device for Supporting Comfortable Drinking, The Institute of Electronics, Information and Communication Engineers, IEICE Technical Report, MVE2012-6, Jun. 15, 2012, pp. 1-4.

Home Network System for Health Care for the Elderly at Home, Systems Control and Information, vol. 47, No. 3, pp. 141-145, 2003.

Ching-Sung, Wang, Smart Voice Water-Cup, Report for the teacher's Industrial and Academic Research Plan Result, the Oriental Institute of Technology, pp. 173-177.

* cited by examiner

LIQUID INGESTING MANAGEMENT SYSTEM

CROSS-REFERENCE TO RELATED APPLICATION AND CLAIM OF PRIORITY

This application claims the benefit of Taiwan Patent Application No. 102112198, filed on Apr. 3, 2013, at the Taiwan Intellectual Property Office, the disclosures of which are incorporated herein in their entirety by reference.

FIELD OF THE INVENTION

The present invention relates to a liquid ingesting management system.

BACKGROUND OF THE INVENTION

It is necessary to drink a proper quantity of water to remain healthy. A normal adult needs about 2000 cc of water per day. However, according to the data, the average quantity of water the typical person drinks every day is about 1200 cc, and even half drink water less than 500 cc at water, which is far from the drinking water ideal. The drinking quantity is related to a person's weight, age, physiological status and climatic environment, such as temperature, humidity or other factors. Drinking water management is very important to health, but it is not easy. Many workers sitting in front of computers, or students spending a long time studying are typically too busy to drink water. Another factor is that staying in a room with air conditioning for a long time affects the ability of natural regulation of a human body. In addition, many patients need to drink a lot of water or strictly control water content in their body; weight management to lose weight and the physiological status of a sportsman relates to water control as well. If there is a convenient drinking water management device which can actively record the quantity of water drunk and remind users to drink water in the proper quantity, it will benefit people's health.

Furthermore, people with a special constitution or those suffering from a particular disease, such as diabetes, must strictly control the ingestion of sugary beverages; some patients only can eat liquid food in limited quantities or take liquid medicine in one day or during a specific period. Therefore, if there is a device that can manage the quantity of liquid ingested, these people will benefit from it.

In order to fulfill this need, a liquid ingesting management system is provided. The particular design in the present invention not only solves the problems described above, but also is easy to be implemented. Thus, the present invention has the utility for the industry.

SUMMARY OF THE INVENTION

The liquid ingesting management system of the present invention can actively remind the user to drink water using a flash of light, such as a light-emitting diode (LED), and inform the user of the ratio relationship between the present drinking quantity and the target drinking quantity. The liquid ingesting management system of the present invention includes a sensing module (monitoring the weight of the liquid, the liquid content, the level of the liquid, the pollution index, the nutrition content index and so on) which can communicate using wireless communication techniques or methods (Bluetooth, Near Field Communication (NFC), Zigbee, ISM sub-G band, WiFi, Infrared ray and so on) to transmit the real-time ingestion record to a personal mobile communication device, a handheld device, a personal digital device or an internet medium, such as Smart Phone, Pad, Notebook, PC and so on. The personal digital device can work in coordination with the application (APP) to synchronously collect the environmental temperature and humidity and the recommended drinking quantity from medical consultation; after the analysis, the user will be reminded to drink water or to temporarily control the quantity of water drunk using the LED on the fluid container of the present invention.

In accordance with an aspect of the present invention, a liquid ingesting management system is provided. The liquid ingesting management system includes a fluid container, a database and a wireless transmit/receive unit. The wireless transmit/receive unit communicates with the fluid container and the database through a wireless technique to access the database and control the fluid container to perform a liquid ingesting management process.

In accordance with another aspect of the preset invention, a fluid container is provided. The fluid container includes a containing body, a sensing module and a wireless communication module. The containing body is configured to contain a liquid, the sensing module is configured in the containing body to obtain sensing information associated with the liquid, and the wireless communication module is configured to provide the sensing information to a user terminal.

In accordance with a further aspect of the present invention, a fluid container is provided. The fluid container includes a containing body and a wireless sensing module. The containing body is configured to contain a liquid, and the wireless sensing module is configured in the containing body to obtain sensing information associated with the liquid and to transmit the sensing information.

In addition, the accessed detailed real-time drinking quantity or other data from the device can be stored via a personal cloud account to record the drinking data every day, every week and every month, so as to build statistical charts as a basis for an everyday drinking plan for the user 105 or as doctor's reference material for diagnosis. The real-time information can be provided to a nurse, a relative, a sports coach, a weight administrator, a health consultant or other relevant personnel. The user will be reminded to ingest the liquid via the LEDs on the fluid container of the present invention or using screen, display and messages in the internet medium 102 or the portable device or transmitted text messages, so as to cause the user to receive real-time reminders without inconvenience.

The above objectives and advantages of the present invention will become more readily apparent to those ordinarily skilled in the art after reviewing the following detailed descriptions and accompanying drawings, in which:

DETAILED DESCRIPTION

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Figure 1:
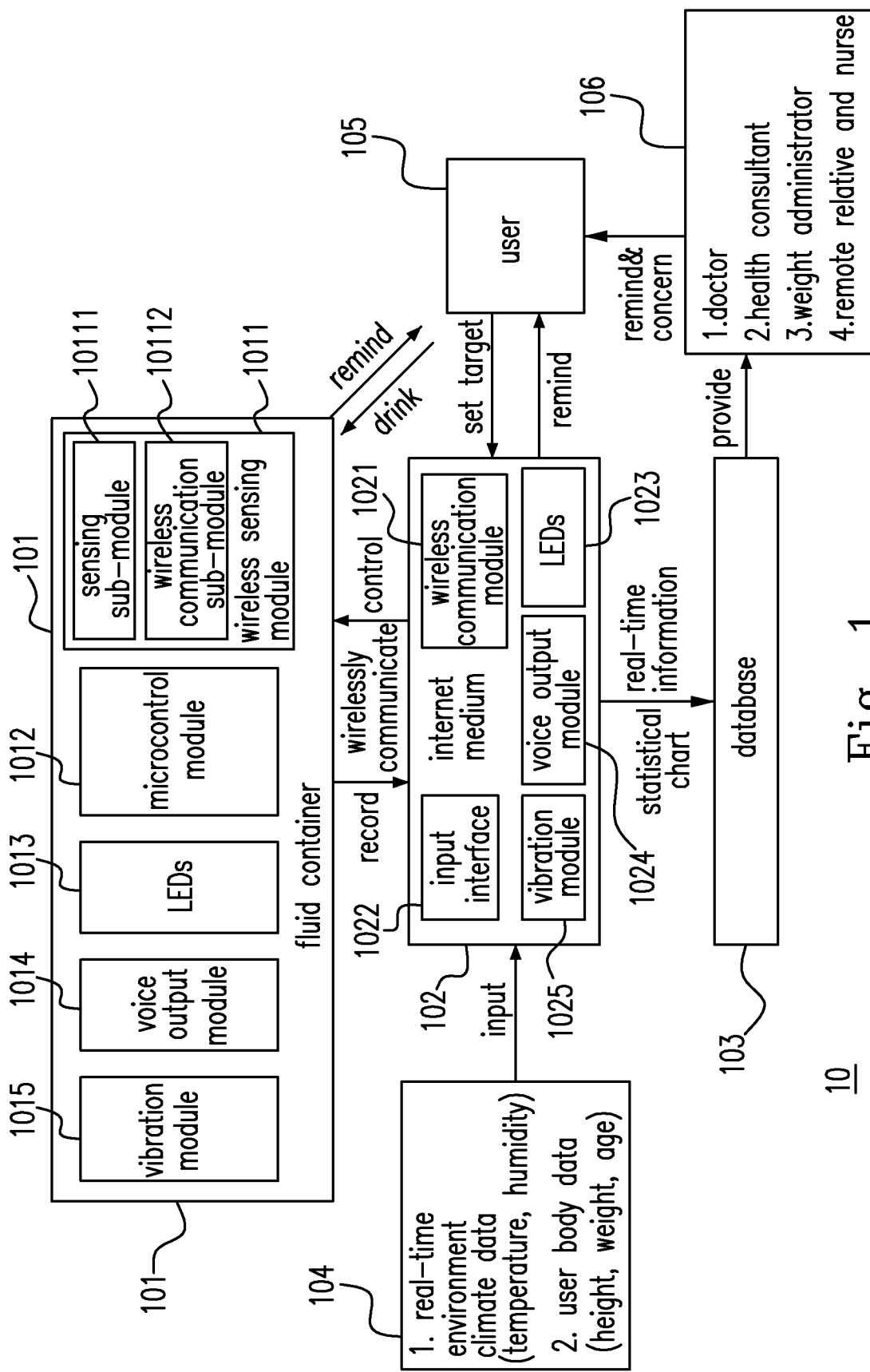
FIG. 1 shows a schematic diagram illustrating a liquid ingesting management system in accordance with an embodiment of the present invention.

Please refer to FIG. 1, which shows a schematic diagram illustrating a liquid ingesting management system 10 in accordance with an embodiment of the present disclosure. The liquid ingesting management system 10 includes a fluid container 101 and an internet medium 102. Preferably, the liquid ingesting management system 10 can include a database 103 on demand.

The fluid container 101 can contain water, beverages, liquid medicine, fluid substances, liquid and so on.

The internet medium 102 communicates with at least one of the fluid container 101 and the database 103 via wireless communication techniques to access the database 103 and to control the fluid container 101, so as to perform a liquid ingesting management process. The liquid ingesting management includes Bluetooth, Near Field Communication (NFC), Zigbee, ISM sub-G band, WiFi, Infrared ray and so on.

The fluid container 101 preferably is a personal drinking equipment or device, such as a (miniature) thermos flask, a kettle, a water cup or container with or without a cover which can contain liquid. The internet medium 102 preferably is a mobile communication device, a handheld device, or a personal digital device, such as Smart Phone, Pad, Notebook, PC and so on.

Figure 2:
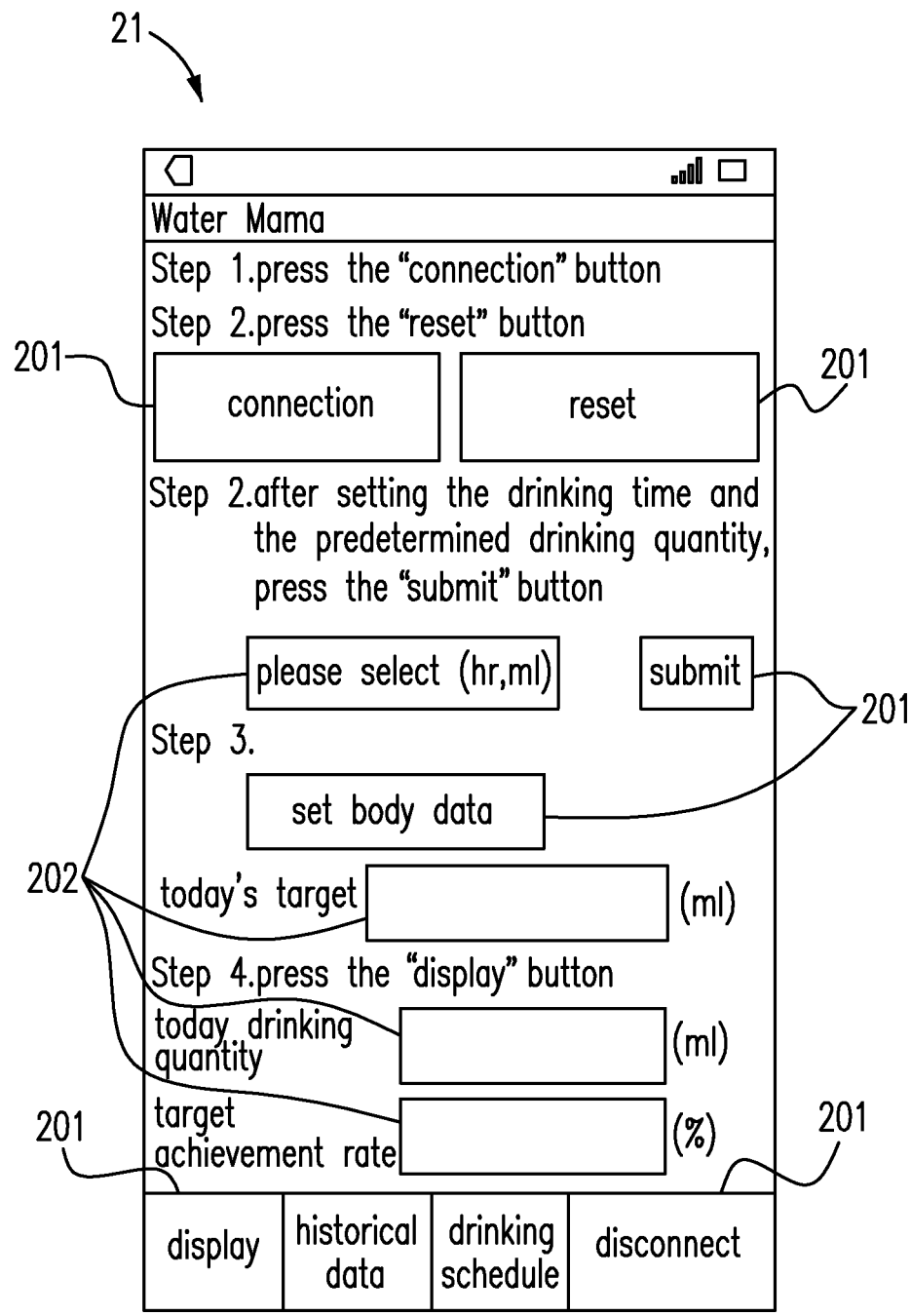
FIG. 2 shows a schematic diagram illustrating the input interface of a portable device APP in accordance with another embodiment of the present invention.

The internet medium 102 includes a wireless communication module 1021 and an input interface 1022. The wireless communication module 1021 is used to provide the wireless communication techniques or methods to communicate with the fluid container 101, and the input interface 1022 is one selected from an APP, an operating system, software, a physical button, a virtual button, a touch interface and a combination thereof. Taking the APP for example, the input interface 1022 can be an APP 20 on a portable device as shown in FIG. 2, and it has a user interface 21, one or more buttons 201 and one or more input frames 202, where the input frame 202 preferably is used to realize the function of input, such as inputting a time reminder to ingest (for example reminding user to drink a specific cc of water every several hours, which may be periodic, nonperiodic or both), user's weight, a predetermined goal, drinking quantity, achievment rate, other information and so on; the buttons 201 can be used to achieve the function of connection or disconnection, so as to activate or end the connection between the internet medium 102 and the fluid container 101, or can be used to submit or set the information input by the user via the input frames 202 and to set body data (for example height, weight, age and so on), or can be further used to switch the display shown by the user interface 21 to provide other information, such as historical data, an ingestion track or schedule, ingestion record, a time reminder, the user weight, the predetermined goal, drinking quantity, achievment rate and various setups. The internet medium 102 or the APP 20 can collect real-time environment climate data (for example the temperature and humidity of the environment) and the body data of the user (for example height, weight, age and so on) 104; after a comparison and analysis of the quantity of water drunk recommended from the medical consultation, the user will be reminded to ingest the liquid needed or temporarily avoid from ingesting the liquid (i.e. controlling the ingestion) via the APP 20 by using screen, display and messages or transmitted text messages. The buttons 201 can be designed as virtual buttons, touch buttons, physical buttons or a combination thereof in response to the type of internet medium 102 or the situation. In addition, the internet medium 102 can receive a management advice, environmental data, user physiological data (body data) or a time reminder, and the drinking time and the drinking quantity are obtained or calculated to remind the user 105 based on the received information above, where the management advice includes medical information, health information, sports information and so on, the environmental data includes temperature, humidity and so on, and the user's physiological data includes height, weight, age, gender, race and so on.

The internet medium 102 preferably includes at least one of LEDs 1023, a voice output module 1024, a vibration module 1025 or a combination thereof. The LEDs 1023, the voice output module 1024, the vibration module 1025 or the combination thereof can perform the reminder function above. For example, the LEDs 1023 can remind the user by lighting, blinking, flashing and the like, and on the condition that the internet medium 102 is a cell phone or a camera, the user can be reminded via the flash lamp and the fill light thereof; the voice output module 1024 preferably includes a buzzer, speaker and so on, the user can be reminded by the voice from the buzzer or speaker or by language, music, ringtone or the like, a pre-recorded voice by relatives and friends can be played to make the user 105 feels pleased about the reminder, and if the user 105 is a child, a voice pre-recorded by the parents can be played to conveniently assist the child; the vibration module 1025 can warn or remind the user 105 via the modes with different times or different frequency. By the above methods, i.e. the visual, auditory, tactile or instinctive methods, to inform the user of the present drinking quantity, the present invention can be commonly used by the hearing impaired or visually impaired, which meets the concept of universal design.

The fluid container 101 includes a wireless sensing module 1011, a microcontrol module 1012 and LEDs 1013, where the wireless sensing module 1011 is configured in the containing body of the fluid container 101 to obtain or measure the information associated with the liquid in the fluid container 101 and to transmit a sensing signal based on the information above, and the internet medium 102 serves as a receiving terminal to receive the sensing signal for reference and management. The sensing signal includes the original liquid quantity, the present liquid quantity, the drunk liquid quantity, the temperature of the liquid, the ambient temperature, the pollution index, the nutrition content index and so on. The pollution index is one selected from an areobic plate count, a heavy metal content, a suspension quantity, a pH value, a chlorine content and a combination thereof, and the nutrition content index is one selected from a sugar content, a heat content, a fat content, a protein content, a vitamin content (e.g. vitamins A, C, D, E, K, B and so on), a micro-element content (e.g. Fe, Zn, Cu, Mn and so on) and a combination thereof. When the environment suddenly changes (for example the original is polluted or it is the first time in a strange environment), it can check on the quality of the drunk fluid. In addition, it can also control the quantity of the nutrition ingested so as to prevent people from physical burden. The wireless sensing module 1011 includes a sensing sub-module 10111 and a wireless communication sub-module 10112. The sensing sub-module 10111 preferably includes one selected from a group consisting of a pressure or liquid level sensor (e.g. a level sensor, a pressure sensor, a load cell, a flow meter, a buoy and so on), a temperature sensor, a XYZ three-axis acceleration sensor, a gyroscope and a combination thereof, so as to sense the original liquid quantity, the present liquid quantity, the drunk liquid quantity and the temperature of the liquid in the fluid container 101, or to sense the temperature of the environment and so on, even to have the function of sensing the pollution index or the nutrition content index, or sensing tilt of the fluid container 101 to exclude certain conditions, such as being knocked over, intentionally pouring the liquid away and so on, so as to enhance the accuracy of the sensed information. The wireless communication sub-module 10112 can transmit the sensing information above to the internet medium 102. The sensed real-time information can be provided to a relevant personnel 106 (e.g. a doctor, a nurse, a relative, a sports coach, a weight administrator, a health consultant and so on) as the reference material for diagnosis or consultation. Alternatively, the user 105 or the relevant personnel 106 can input an external signal or a user command via the input interface 1022 of the APP 20 to set, manage or control the fluid container 101, for example setting the drinking time to remind the user 105, when to remind, the reminding interval and the drinking quantity, and even setting or controlling the opening of the fluid container 101 to be closed or opened. The fluid container 101 preferably includes LEDs 1013, a voice output module 1014 and a vibration module 1015. The microcontrol module 1012 can be used to set, manage or control the fluid container 101. Specifically, via the microcontrol module 1012, the LEDs 1013, the voice output module 1014, the vibration module 1015 or the combination thereof can be controlled to remind the user to drink the proper quantity of liquid, or the opening of the fluid container 101 can be set or controlled to be opened or closed so as to control the ingestion or injection of the liquid for the user 105. For example, if the user is a child, it can forbid the child to drink sugary beverages after the user 105 brushes his teeth. In addition, the LEDs 1013 can remind the user 105 by lighting, blinking, flashing and the like; the voice output module 1014 includes a buzzer, speaker and so on, the user 105 can be reminded by the voice from the buzzer or speaker or by speech, music, ringtone or the like from the speaker, the pre-recorded voice by relatives and friends can be played to make the user 105 feel pleased about the reminder, or the voice pre-recorded by the parents can be played to conveniently assist the child; the vibration module 1015 can warn or remind the user 105 via the modes with different times or different frequency. By the above methods, i.e. the visual, auditory, tactile or instinctive methods, to inform the user of the present drinking quantity, the present invention can be commonly used by the hearing impaired or visually impaired, which meets the concept of universal design. The microcontrol module 1012 can also receive the sensing information above, and perform a water quantity calculation or a liquid ingesting management calculation based thereon, so as to control the LEDs 1013, the voice output module 1014 and the vibration module 1015 to generate a prompt.

Figure 3:
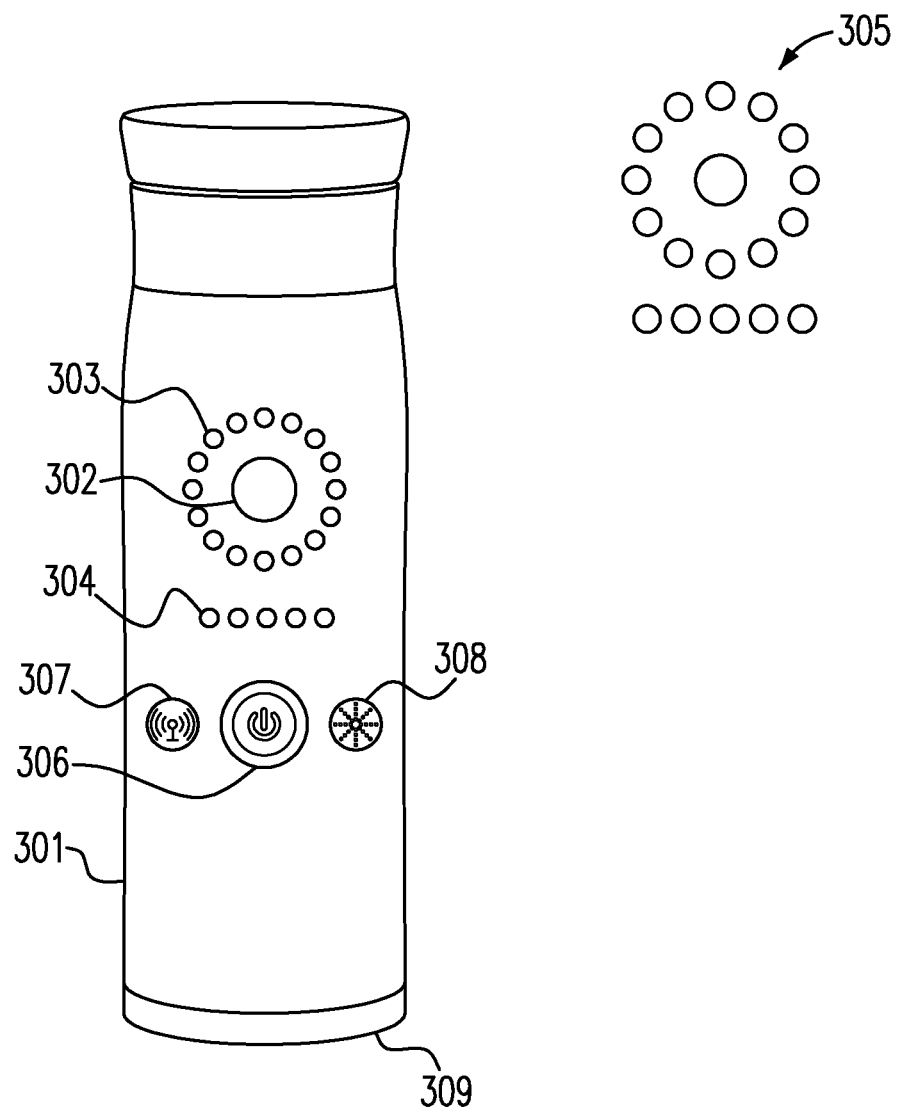
FIG. 3 shows a schematic diagram illustrating a fluid container in accordance with another embodiment of the present invention.

Please refer to FIG. 3, which shows a schematic diagram illustrating a fluid container 301 in accordance with another embodiment of the present disclosure. The fluid container 301 is one type of the fluid container 101, and includes a signal light 305 (consisting of LEDs 302, 303 and 304), a voice output module 308, a vibration module (not shown) and a bottom 309, so as to display or remind the user of the relevant ingestion management messages to realize the reminding methods or functions above.

For example, when the APP 20 or the microcontrol module 1012 calculate the time the user 105 needs to drink the liquid in the fluid container 301, the LED 302 can remind the user 105 by lighting, blinking, flashing and the like that it's time to drink; when the user 105 drinks a specific quantity of the liquid, the LED 302 will turn off the light, or stop blinking or flashing; if the user 105 does not drink the liquid, the LED 302 will increase the frequency of the flashing or enhance the brightness of the lighting so as to make the user 105 aware of it. The plurality of LEDs 303 can be used to remind the user 105 of the quantity of the drunk liquid, for example every lit LED 302 or every dark LED 302 represents a specific drunk quantity (such as 120 cc); the plurality of the LEDs 304 can be used to display the quantity of the liquid to drink this time, for example every lit LED 304 or every dark LED 304 represents a specific quantity the user 105 needs to drink (such as 100 cc) so as to remind the user 105 of the ratio relationship between the present drinking quantity and the target drinking quantity. The preferable arrangement and configuration is that the plurality of LEDs 304 are arranged in one line and selected from first color LEDs (such as blue) and many small-sized LEDs 303 are configured around the large-sized LED 302, where the LEDs 303 are selected from a second color LEDs (such as white) and the LED 302 is preferably selected from a third color LED (such as red). Each of the plurality of the LEDs 304 can be different color LEDs, and the function of displaying the quantity of the liquid can be realized using the combination of brightness and darkness of the different color LEDs. By the same token, the plurality of the LEDs 303 can realize the functions using different color LEDs.

The voice output module 308 can be a buzzer or a speaker built in or outside the fluid container 301 to produce voices or to play speech, music, ringtone or the like, so as to remind the user 105. The fluid container 301 can warn or remind the user 105 via the modes at different times or different frequency by a vibration module.

The cladding material of the fluid container 301 is preferably transparent material or translucent material, such that the necessary electric elements, vibration module and so on can be configured under the condition of not damaging the fluid container 301. In addition, a portion of the transparent or translucent cladding material corresponding to the electric elements can undergo mirror surface processing to hide the circuits of the electric elements, such that only the LEDs or the elements with the visual indication function can be seen to enhance the attractive appearance of the fluid container 301. Furthermore, in the embodiment, the fluid container 301 further includes a switch 306 and a wireless communication switch 307. The switch 306 is configured to control the power of the fluid container 301, the switch can be a touch switch or a push switch with an LED indicating whether the power is on or not, and the switch 306 can be selectively configured in a recessed area of the surface of the fluid container 301 to avoid an unintentional press. The wireless communication switch 307 is configured to turn on or off the wireless communication function (such as Bluetooth, Near Field Communication (NFC), Zigbee, ISM sub-G band, WiFi, Infrared ray and so on), the real-time data is transmitted to the internet medium 102, and the best drinking time and drinking quantity are calculated using APP 20 so as to control when the LEDs 302, 303 and 304 light. The wireless communication switch 307 further includes a indicator light to indicate the status whether the wireless communication function is on or off. In addition, the vibration module 1015, the microcontrol module 1012 or the wireless sensing module 1011 is preferably configured in the bottom 309.

The database 103 is preferably a cloud database, the accessed drinking record (such as an ingestion time, an ingestion quantity, an ingestion track and an ingestion statistical chart) or data can be immediately or later transmitted to the database 103 via the internet medium 102 or the APP 20, the database 103 is preferably configured to have a personal cloud account to store the data, the personal cloud account corresponds to the user 105 to record the drinking track or schedule day by day, week by week and month by month, so as to build the statistical chart as a basis for an everyday drinking plan for the user 105 or as a doctor's reference material for diagnosis. The real-time information can be provided to the relevant personnel 106 (e.g. a doctor, a nurse, a relative, a sports coach, a weight administrator, a health consultant and so on), and the relevant personnel 106 preferably performs searching or inquiry via the APP and at the same time, can also monitor much of users' real-time information to make oberving, reminding or caring for the user easy. The user will be reminded to ingest the liquid via the LEDs on the fluid container 101 or using screen, display and messages in the internet medium 102 or the portable device or transmitting text messages, so as to cause the user to be aware of the real-time reminders. In addition, the database 103 also can be partially or wholly configured in one selected from a group consisting of the fluid container 101, the internet medium 102, a storage medium and a combination thereof.

Embodiments

1. A liquid ingesting management system comprises a fluid container; a database; and a wireless transmit/receive unit communicating with the fluid container and the database through a wireless technique to access the database and control the fluid container to perform a liquid ingesting management process.
2. The liquid ingesting management system of Embodiment 1, wherein the wireless transmit/receive unit is an internet medium.
3. The liquid ingesting management system of Embodiment 1 or 2, wherein the internet medium is a handheld device, wherein the handheld device includes a wireless communication module and an input interface so as to communicate with the fluid container and the database to access the database and to perform one being selected from a group consisting of setting, managing and controlling the fluid container to perform the liquid ingesting management process.
4. The liquid ingesting management system of any one of Embodiments 1-3, wherein the database is a cloud database, and the internet medium is further configured to receive a user command to set a drinking time and a drinking quantity.
5. The liquid ingesting management system of any one of Embodiments 1-4, wherein the internet medium further includes an input interface, the user command is input via the input interface, and the input interface is one being selected from a group consisting of a software, an operating system, an application, a button, a touch panel and a combination thereof
6. The liquid ingesting management system of any one of Embodiments 1-5 further comprises a storage medium, wherein the database is further configured in one selected from a group consisting of the fluid container, the internet medium and the storage medium.
7. The liquid ingesting management system of any one of Embodiments 1-6, wherein the fluid container is a personal drinking equipment containing a liquid and having a light device, the database is configured to store information regarding the liquid and a user, the database is further configured to store an account of the user, the information is associated with the account, and the light device is configured to remind the user based on the information.
8. The liquid ingesting management system of any one of Embodiments 1-7, wherein the information includes an ingestion time, an ingestion quantity, an ingestion track and an ingestion statistical chart.
9. The liquid ingesting management system of any one of Embodiments 1-8, wherein the light device further includes a first light-emitting diode (LED) and a second LED which are configured to provide a first message and a second message respectively.
10. The liquid ingesting management system of any one of Embodiments 1-9, wherein the light device is further configured to represent a present drinking quantity.
11. The liquid ingesting management system of any one of Embodiments 1-10, wherein the internet medium is configured to receive one selected from a group consisting of a management advice, environmental data, a user physiological data, a time reminder, sensing data and a combination thereof, so as to obtain a drinking time and a drinking quantity based thereon.
12. The liquid ingesting management system of any one of Embodiments 1-11, wherein the management advice includes one selected from a group consisting of medical information, health information, sports information and a combination thereof, the environmental data include a temperature, a humidity and a combination thereof, the user physiological data include a height, a weight, an age, a gender, a race and a combination thereof, and the sensing data include a pollution index, a nutrition index and a combination thereof
13. The liquid ingesting management system of any one of Embodiments 1-12, wherein the pollution index is one selected from a group consisting of an areobic plate count, a heavy metal content, a suspension quantity, a pH value, a chlorine content and a combination thereof, and the nutrition index is one selected from a group consisting of a sugar content, a heat content, a fat content, a protein content, a vitamin content, a micro-element content and a combination thereof
14. A fluid container, comprises a containing body configured to contain a liquid; a sensing module configured in the containing body to obtain sensing information associated with the liquid; and a wireless communication module configured to provide the sensing information to a user terminal.
15. The fluid container of Embodiment 14 further comprises a light-emitting diode configured to show one of the sensing information and a reminder information; and a control module configured to control the light-emitting diode based on one of the sensing information and an external signal.
16. The fluid container of Embodiment 14 or 15, wherein the control module is further configured to perform at least one of a water quantity calculation and a liquid ingesting management calculation.
17. The fluid container of any one of Embodiments 14-16, wherein the sensing module is one selected from a group consisting of a liquid level sensor, a temperature sensor, a three-axis acceleration sensor, a gyroscope and a combination thereof
18. The fluid container of any one of Embodiments 14-17, wherein the terminal is one selected from a group consisting of a mobile communication device, a notebook computer and a personal computer.

19. A fluid container, comprises a containing body configured to contain a liquid; and a wireless sensing module configured in the containing body to obtain sensing information associated with the liquid and to transmit the sensing information.

20. The fluid container of Embodiment 19, wherein the wireless sensing module further comprises a sensing sub-module configured to obtain the sensing information; and a wireless communication sub-module configured to provide the sensing information to a user terminal.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A liquid ingesting management system for managing sensing information associated with a liquid to be ingested by a user, comprising:
    a portable drinking container comprising:
        a containing body configured to contain the liquid to be ingested by the user,
        a wireless sensing module integrated within the containing body and configured to perform the following:
            generating the sensing information associated with the liquid, with the sensing information including a current level and temperature of the liquid within the containing body, and
            transmitting the sensing information;
    a database configured to store information regarding a recommended quantity of liquid to be ingested by the user;
    a portable wireless transmit/receive unit to be carried by the user and configured to communicate in real time with the portable drinking container and the database to perform a liquid ingesting management process comprising:
        determining a quantity of liquid ingested by the user based on the current level of the liquid within the containing body,
        comparing the quantity of liquid ingested by the user to the recommended quantity of liquid to be ingested by the user, and
        reminding the user to ingest more liquid if the quantity of liquid ingested is less than the recommended quantity of liquid to be ingested; and
    a light device including first, second and third light-emitting diodes (LEDs), wherein the first LED is configured to remind in real-time the user of ingesting the liquid, the second LED includes a first plurality of LEDs and indicates how much the user has drunk of the liquid through a number of lit or dark LEDs in the first plurality of LEDs, each of which represents a specific drunk quantity, and the third LED indicates how much of the liquid the user needs to ingest currently.

2. The liquid ingesting management system as claimed in claim 1, wherein the portable wireless transmit/receive unit is an internet medium.

3. The liquid ingesting management system as claimed in claim 2, wherein the internet medium is a handheld device, wherein the handheld device includes a wireless communication module and an input interface so as to communicate with the portable drinking container and the database to access the database and to perform one being selected from a group consisting of setting, managing and controlling the portable drinking fluid container to perform the liquid ingesting management process.

4. The liquid ingesting management system as claimed in claim 3, wherein the database is a cloud database, and the internet medium is further configured to receive a user command to set a drinking time and a drinking quantity.

5. The liquid ingesting management system as claimed in claim 4, wherein the internet medium further includes an input interface, the user command is input via the input interface, and the input interface is one being selected from a group consisting of a software, an operating system, an application, a button, a touch panel and a combination thereof.

6. The liquid ingesting management system as claimed in claim 2 further comprising a storage medium, wherein the database is further configured in one selected from a group consisting of the portable drinking container, the internet medium and the storage medium.

7. The liquid ingesting management system as claimed in claim 2, wherein the portable drinking container is a personal drinking equipment containing the liquid and having the light device, the database is configured to store information regarding the liquid and the user, the database is further configured to store an account of the user, the information is associated with the account, and the light device is configured to remind the user based on the information.

8. The liquid ingesting management system as claimed in claim 7, wherein the information includes an ingestion time, an ingestion quantity, an ingestion track and an ingestion statistical chart.

9. The liquid ingesting management system as claimed in claim 1, wherein the first plurality of LEDs surround first LED.

10. The liquid ingesting management system as claimed in claim 1, wherein the first LED has a size larger than each of the first plurality of LEDs, and the third LED includes a second plurality of LEDs and indicates how much of the liquid the user needs to ingest currently through a second number of lit or dark LEDs in the second plurality of LEDs, each of which represents a specific quantity the user needs to ingest so as to remind the user of a ratio relationship between the presently drunk quantity and a target drinking quantity.

11. The liquid ingesting management system as claimed in claim 1, wherein the portable wireless transmit/receive unit receives management advice, environmental data, a user physiological data, a time reminder and sensing data, so as to obtain a drinking time and a drinking quantity based thereon to remind the user,
    with the management advice including one selected from a group consisting of medical information, health information, sports information and a combination thereof,
    with the environmental data including a temperature, a humidity and a combination thereof,
    with the user physiological data including, a weight, an age, a gender, a race and a combination thereof, and
    with the sensing data including a pollution index, a nutrition index and a combination thereof.

12. The liquid ingesting management system as claimed in claim 11, wherein the pollution index is one selected from a group consisting of an aerobic plate count, a heavy metal content, a suspension quantity, a pH value, a chlorine content and a combination thereof, and the nutrition index is one selected from a group consisting of a sugar content, a heat content, a fat content, a protein content, a vitamin content, a micro-element content and a combination thereof.

13. A portable drinking container for managing sensing information associated with a liquid to be ingested by a user, comprising:
- a containing body configured to contain the liquid to be ingested by the user;
- a wireless sensing module integrated within the containing body and configured to generate the sensing information associated with the liquid, with the sensing information including a current level and temperature of the liquid within the containing body;
- a wireless communication module configured to perform the following:
  - transmitting the sensing information to a user terminal having information regarding a recommended quantity of liquid to be ingested by the user, and
  - receiving from the user terminal reminder information for the user to ingest more liquid if the quantity of liquid consumed is less than a recommended quantity of liquid to be consumed; and
- a light device including first, second and third light-emitting diodes (LEDs), wherein the first LED is configured to remind in real-time the user of ingesting the liquid, the second LED includes a first plurality of LEDs and indicates how much the user has drunk of the liquid through a number of lit or dark LEDs in the first plurality of LEDs, each of which represents a specific drunk quantity, and the third LED indicates how much of the liquid the user needs to ingest currently.

14. The portable drinking container as claimed in claim 13, further comprising:
- a control module configured to control the light device.

15. The portable drinking container as claimed in claim 14, wherein the control module is further configured to perform at least one of a water quantity calculation and a liquid ingesting management calculation.

16. The portable drinking container as claimed in claim 14, wherein the user terminal is one selected from a group consisting of a mobile communication device, a notebook computer and a personal computer.

17. A portable drinking container for managing sensing information associated with a liquid to be ingested by a user, comprising:
- a containing body configured to contain the liquid to be ingested by the user;
- a wireless sensing module integrated within the containing body and comprising:
  - a sensing sub-module configured to generate the sensing information associated with the liquid, with the sensing information including a current level and temperature of the liquid within the containing body; and
  - a wireless communication sub-module configured to perform the following:
    - transmitting the sensing information to a user terminal having information regarding a recommended quantity of liquid to be ingested by the user, and
    - receiving from the user terminal reminder information for the user to ingest more liquid if the quantity of liquid consumed is less than a recommended quantity of liquid to be consumed; and
- a light device including first, second and third light-emitting diodes (LEDs), wherein the first LED is configured to remind in real-time the user of ingesting the liquid, the second LED includes a first plurality of LEDs and indicates how much the user has drunk of the liquid through a number of lit or dark LEDs in the first plurality of LEDs, each of which represents a specific drunk quantity, and the third LED indicates how much of the liquid the user needs to ingest currently.

* * * * *